(12) United States Patent
Berberich et al.

(10) Patent No.: US 8,524,172 B2
(45) Date of Patent: Sep. 3, 2013

(54) AUTOMATIC CALIBRATION OF A STAINING DEVICE

(75) Inventors: Markus Berberich, Heidelberg (DE); Christian Wilke, Rimbach (DE)

(73) Assignee: Leica Biosystems Nussloch GmbH, Nussloch (DE)

(*) Notice: Subject to any disclaimer, the term of this patent is extended or adjusted under 35 U.S.C. 154(b) by 74 days.

(21) Appl. No.: 13/178,588

(22) Filed: Jul. 8, 2011

(65) Prior Publication Data

US 2012/0009101 A1 Jan. 12, 2012

(30) Foreign Application Priority Data

Jul. 9, 2010 (DE) .................... 10 2010 036 317

(51) Int. Cl.
*A61B 10/00* (2006.01)
(52) U.S. Cl.
USPC ............. 422/536; 422/63; 422/64; 422/65; 422/66; 422/67; 436/180
(58) Field of Classification Search
USPC .............. 422/50, 63–67, 536; 436/180
See application file for complete search history.

(56) References Cited

U.S. PATENT DOCUMENTS

| | | | |
|---|---|---|---|
| 3,903,908 A | 9/1975 | Logue et al. | |
| 5,601,650 A | 2/1997 | Goldbecker et al. | |
| 6,626,224 B1 * | 9/2003 | Ljungmann | 156/557 |
| 8,158,061 B2 * | 4/2012 | Shah et al. | 422/65 |
| 2005/0250211 A1 | 11/2005 | Reinhardt et al. | |
| 2006/0088928 A1 | 4/2006 | Sweet et al. | |
| 2010/0170336 A1 | 7/2010 | Berberich et al. | |

FOREIGN PATENT DOCUMENTS

WO 9726541 A1 7/1997

OTHER PUBLICATIONS

United Kingdom Intellectual Property Office, Combined Search and Examination Report in Application No. GB1111224.0, dated Oct. 12, 2011.

* cited by examiner

*Primary Examiner* — Jyoti Nagpaul
(74) *Attorney, Agent, or Firm* — Hodgson Russ LLP

(57) ABSTRACT

A sensor device (45) for calibrating a staining device (20) has a coupling unit (46) which is configured to be attachable to a transport device (22) of the staining device (20). A sensor unit (48) of the sensor device (45) is adapted to detect the presence of components of the staining device (20).

6 Claims, 4 Drawing Sheets

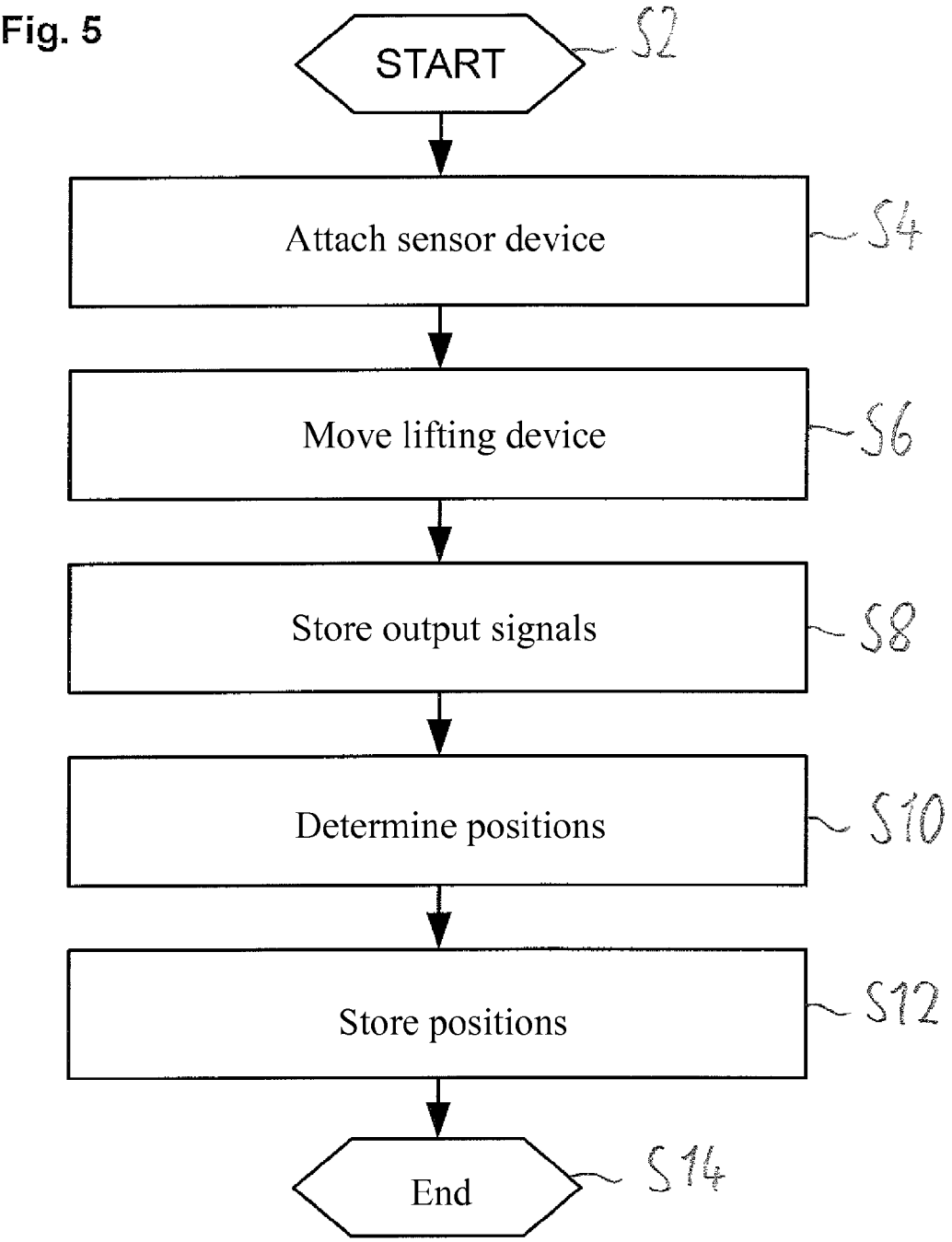

AUTOMATIC CALIBRATION OF A STAINING DEVICE

CROSS REFERENCE TO RELATED APPLICATIONS

This application claims priority of German patent application number 10 2010 036 317.0 filed Jul. 9, 2010, the entire disclosure of which is incorporated by reference herein.

FIELD OF THE INVENTION

The present invention relates to a sensor device for calibrating a staining device and to a staining device. The staining device includes a transport device by means of which sample baskets can be moved to different components within the staining device. Moreover, the present invention relates to a method for calibrating the staining device.

BACKGROUND OF THE INVENTION

Samples, in particular tissue samples to be examined using a microscope, are routinely stained using staining devices, so that structures of the samples can be better seen in the microscopic image than in the case of unstained samples. For sample staining, a staining device includes two or more containers in which identical, similar or different process media are stored. The samples to be stained are immersed in the process media, where they remain for residence times which are dependent on the process step, the process medium, and on the sample to be stained. Once the predetermined residence time has elapsed, the samples are withdrawn from the container and transferred to the next container by means of a transport system. Depending on the staining method and/or the sample, the samples are in this manner successively immersed in a plurality of containers filled with process media. Moreover, the samples may be dried before, between or after the aforementioned steps, using an oven. For example, moist sections of paraffin-embedded tissue samples placed on slides may be dried in the oven, thereby evaporating the moisture and partially melting the paraffin, which improves the adherence of the tissue samples to the slides.

The containers and the oven, if provided, are positioned within the staining device during assembly thereof. After that, the containers and/or the oven may be replaced, for example, for purposes of repair. Moreover, optional components, such as the oven, cuvettes, or additional containers, may be added later. Further, the transport device, its attachment and suspension arrangement, as well as a lifting device of the transport device have manufacturing tolerances. In order for the staining operation to function properly after replacement or installation of components and despite the tolerances, the staining device is calibrated. During calibration, the exact positions of the containers and the oven in the staining device are determined, taking into account the tolerances, and stored in a processing unit. The staining process and, in particular, the transport system of the staining device can then be controlled by the processing unit.

SUMMARY OF THE INVENTION

It is an object of the present invention to provide a sensor device for calibrating a staining device, a staining device, and a method for calibrating the staining device, which will allow easy calibration of the staining device.

This object is achieved by the features of the independent claims. Advantageous embodiments are set forth in the dependent claims.

A first aspect of the present invention resides in a sensor device for calibrating a staining device. The sensor device includes a coupling unit and a sensor unit. The coupling unit is configured to be attachable to a transport device of the staining device. The sensor unit is adapted to detect the presence of components of the staining device. The sensor device is also able to determine the positions of such components.

In order to calibrate the staining device, the sensor device can be attached to the transport device in place of a sample basket for holding samples. The sensor device can then be moved to different components of the staining device. Once the sensor device detects the presence of a component, the position of corresponding component can be determined based on the known current position of the transport system. The positions of the individual components may be stored, so that they are precisely known during further operation of the staining device.

In a specific embodiment, the sensor unit operates using acoustic, optical or tactile sensing techniques. In other words, the sensor unit includes a device for generating sound waves, such as ultrasound, and a sensor for receiving sound waves reflected from the components, or the sensor unit includes a laser and a photosensitive element capable of detecting laser beams reflected from the components, or the sensor unit includes touch-sensitive elements which, upon contact with components of the staining device, cause corresponding output signals to be produced in the sensor unit. The device for generating sound waves and/or the sensor for receiving the sound waves include, for example, a piezoelectric ceramic material or a piezoelectric plastic material.

In another embodiment, the sensor unit includes a base element, a sensor lever, and a sensor circuit. The sensor lever is fixedly secured to the base element. The sensor unit may be configured in the manner of a control stick or joystick, so that movement of the sensor lever can be detected in a similar way as that of a joystick. The position of the sensor lever can be detected by the sensor circuit. When the sensor lever hits the components of the staining device as the sensor device is moved, then this can be detected by the sensor circuit, for example by way of microswitches of the sensor circuit which are acted upon by the sensor lever.

Alternatively, the sensor unit may be capable of detecting a force acting on the sensor lever. For example, the sensor lever may be provided with one or more strain gauges capable of detecting bending of the sensor lever. Such bending deformations are then reflected in the output signal of the sensor unit, and indicate contact of the sensor lever with one of the components, in particular with a wall of the corresponding component.

Since the current position of the transport system, and thus the position of the sensor device, are known at all times, the positions of the components can be determined based on the output signals of the sensor unit. These positions can then be stored. After that, the positions of the components are known.

A second aspect of the present invention resides in the staining device, which includes the transport device to which the sensor device is attached. The staining device further includes a plurality of components disposed in different locations within the staining device. A calibration unit is capable of driving the transport device to move the sensor device to the different locations of the staining device. The components of the staining device include, for example, a plurality of containers which are filled, or at least fillable, with process media for processing the samples. Moreover, the components may include an oven for drying the samples, or cuvettes, in particular heated cuvettes. The positions of the containers and/or of the oven can be determined by means of the sensor device, so that the sample baskets can be precisely placed into the containers containing the process media, or into the oven, during subsequent operation.

A third aspect of the present invention resides in a method for calibrating the staining device. For this purpose, the sensor device is attached to the transport device of the staining device. The transport device moves the sensor device to different locations within the staining device. The sensor device is used to detect where predetermined components of the staining device are located within the staining device.

In a specific embodiment, the transport device moves the sensor device over and/or through the staining device in such a manner that the sensor lever of the sensor device successively hits the different components and/or hits the same components repeatedly, thereby influencing an output signal of the sensor unit. In particular, the sensor unit detects the current position of the sensor lever, which changes upon contact with the components, or the force exerted on the sensor lever upon contact with the components. The arrangement of the components within the staining device is determined based on the output signal of the sensor unit and the current position of the sensor device.

BRIEF DESCRIPTION OF THE DRAWINGS

Exemplary embodiments of the present invention are described in more detail below with reference to the schematic drawings, in which:

FIG. 5 is a flow chart of a program for calibrating the staining device.

Elements having the same design or function are identified by the same reference numerals throughout the figures.

DETAILED DESCRIPTION OF THE INVENTION

Figure 1:
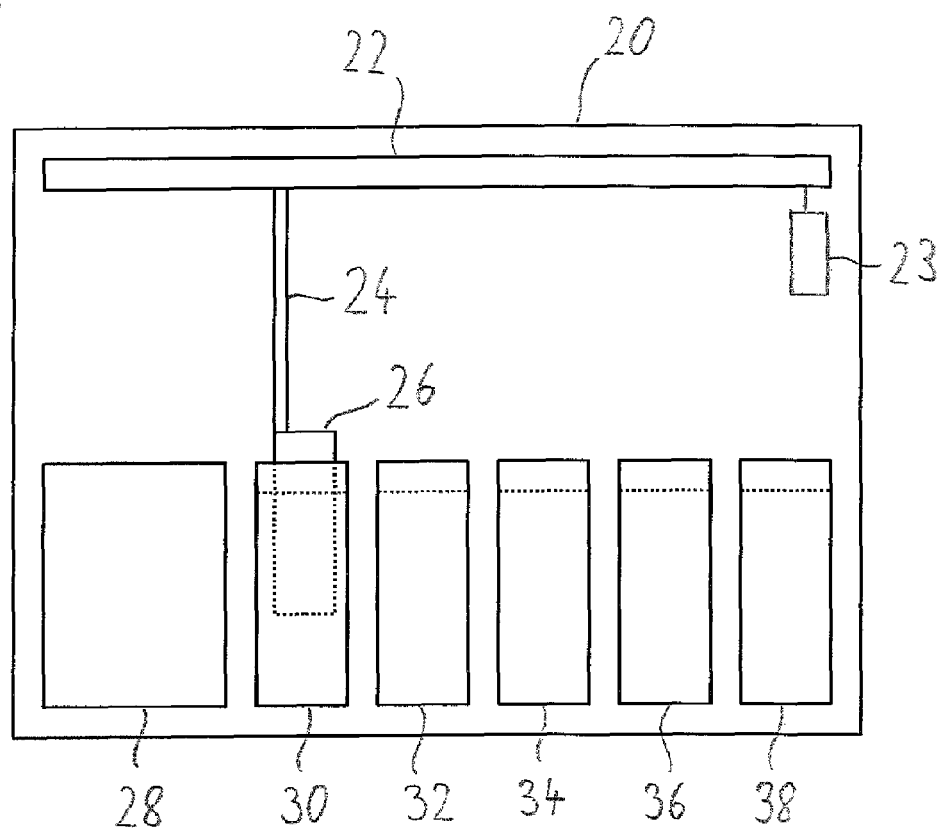
FIG. 1 is a side view of a staining device.

FIG. 1 shows a schematic side view of a staining device 20. Staining device 20 is suitable for staining samples, in particular tissue samples, for subsequent examination under a microscope. Staining device 20 includes a transport device 22 having a lifting device 24. Attached to lifting device 24 is a sample basket 26, which is partially located in a first container 30. Besides first container 30, staining device 20 includes additional components or modules, in particular an oven 28 and a second container 32, a third container 34, a fourth container 36, and a fifth container 38. Containers 30, 32, 34, 36, 38 are filled with different process media for cleaning and staining the samples in sample basket 26. Sample basket 26 can be successively immersed in oven 28 and/or in containers 30, 32, 34, 36, 38 by means of transport device 22, in particular by lifting device 24.

Figure 2:
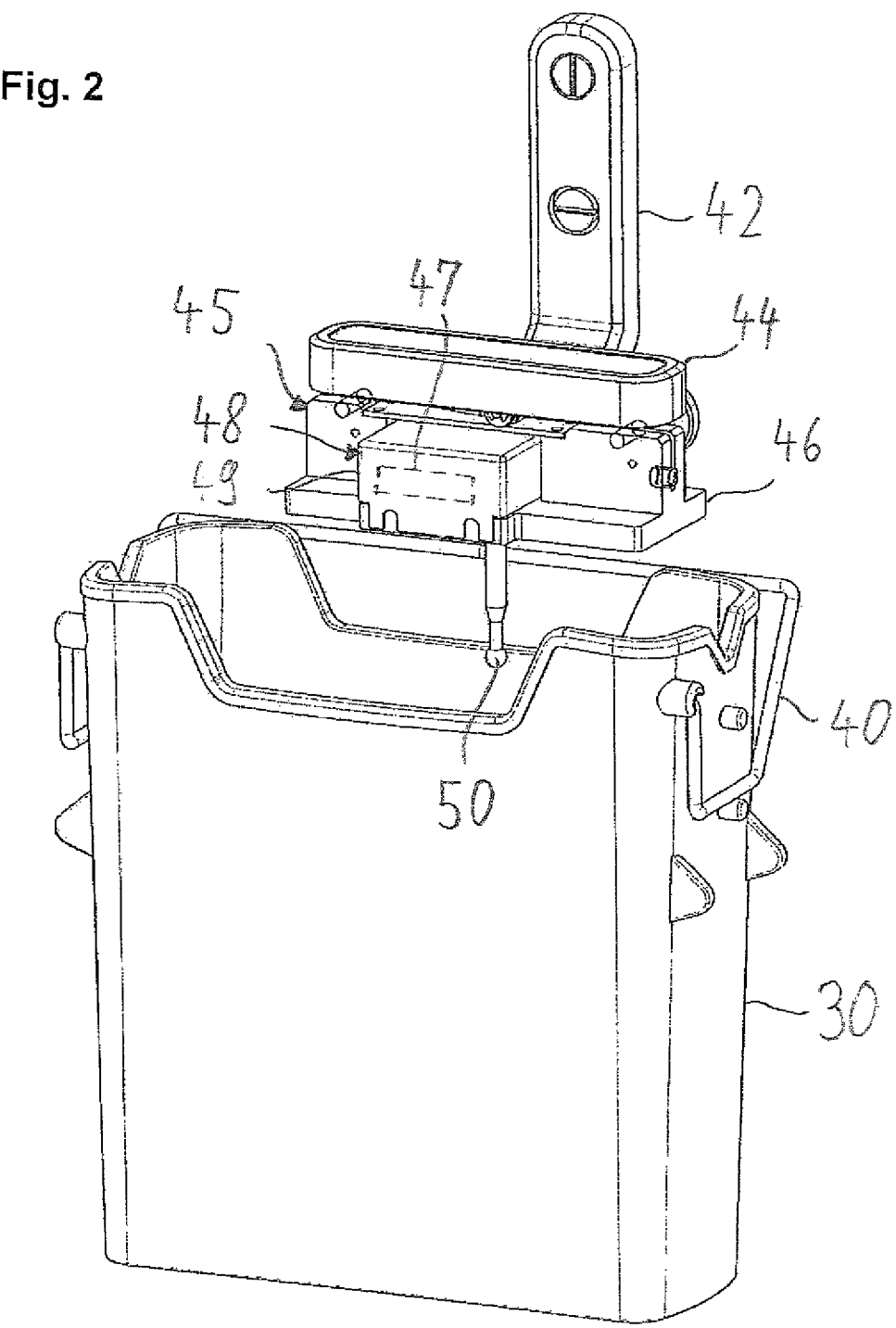
FIG. 2 is a perspective view showing a sensor device and a sample basket of the staining device.

FIG. 2 shows, by way of example, one of containers 30, 32, 34, 36, 38, which has a handle 40 secured thereto. By means of handle 40, sample basket 26 can be lifted, removed from or placed into staining device 20. A holder 42 is mounted to lifting device 24 (not shown in FIG. 2). Holder 42 is fixedly connected to a coupling member 44. Coupling member 44 is configured such that sample basket 26 can be attached thereto. To this end, coupling member 44 includes, for example, one or more latch means which may cooperate with corresponding mating latch means on the sample basket. However, a sensor device 45 is attached to coupling member 44 in place of sample basket 26.

Sensor device 45 includes a sensor unit 48 and a coupling unit 46 for attachment to coupling member 44 of transport device 22. Coupling unit 46 includes means, such as latch means, by which coupling unit 46 can be fixedly secured to coupling member 44. Sensor unit 48 includes a sensor lever 50, which is fixedly secured to a base element 49 of sensor unit 48. Sensor unit 48 further includes a sensor circuit 47 by means of which a position of sensor lever 50 or a force acting on sensor lever 50 can be detected. As an alternative to sensor lever 50, which allows tactile sensing of the position of the components, it is also possible to provide a sensor which operates using optical or acoustic sensing techniques. For example, an optical sensor unit may be provided, for example, in the form of a laser and a photosensitive sensor element for detecting the laser beam reflected from the components. An acoustic sensor unit may be provided, for example, in the form of an ultrasound source and a piezoelectric ceramic or plastic material for detecting the sound waves reflected by the components of the staining device.

Figure 3:
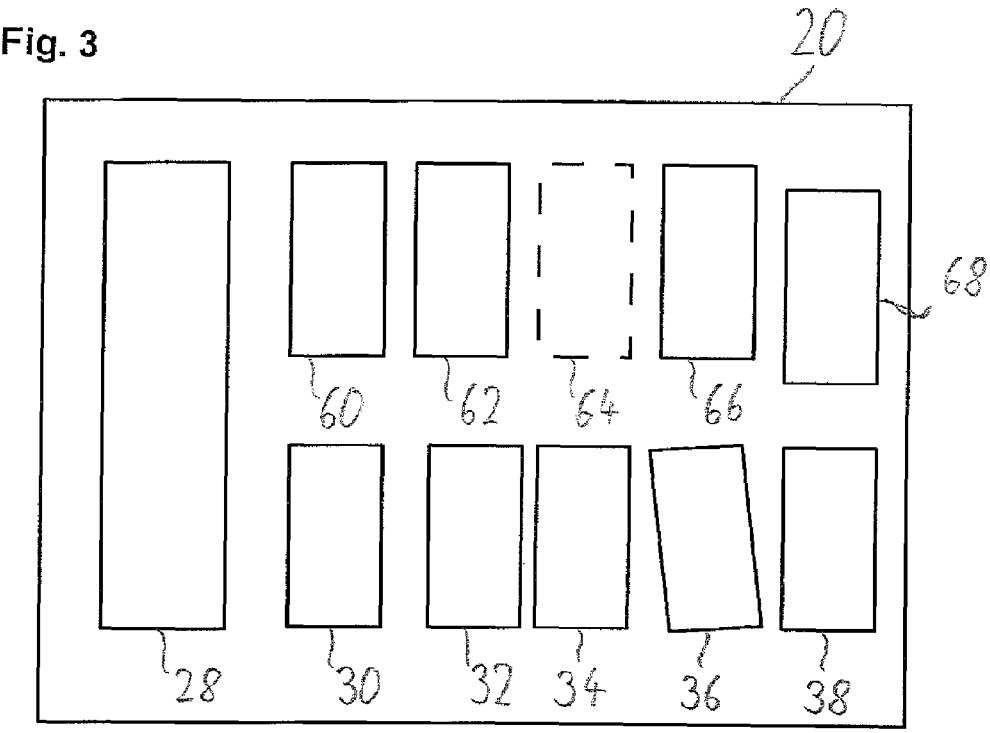
FIG. 3 is a plan view of the staining device.

FIG. 3 shows a plan view of a staining device 20, showing that a sixth container 60, a seventh container 62, an empty receiving space 64 for a further container, an eighth container 66 and a ninth container 68 are arranged in staining device 20. Containers 30 through 38 and 60 through 68 are placed into staining device 20 during assembly thereof. In order to facilitate emptying, cleaning, and servicing of containers 30 through 38 and 60 through 68, said containers can be removed from and replaced into staining device 20. To this end, staining device 20 has provided therein a plurality of receiving spaces; specifically, one receiving space for each of containers 30 through 38 and 60 through 68. An empty receiving space 64 is not occupied. Further, ninth container 68 is somewhat displaced toward fifth container 38 within staining device 20. Fourth container 36 is slightly rotated out of position within staining device 20, and second container 32 is somewhat displaced toward third container 34. The irregular arrangement of containers 30 through 38 and 60 through 68 within staining device 20 may be due, for example, to manufacturing tolerances, particularly of the receiving spaces, or to the negligence of a user.

Transport device 22, its attachment and suspension arrangement and/or its lifting device 24, may also have manufacturing tolerances, so that transport devices 22 of different staining devices of identical design may be located at slightly different positions within staining device 20. Moreover, the motion amplitudes of different transport devices 22 of identical design may differ for identical control inputs.

Figure 4:
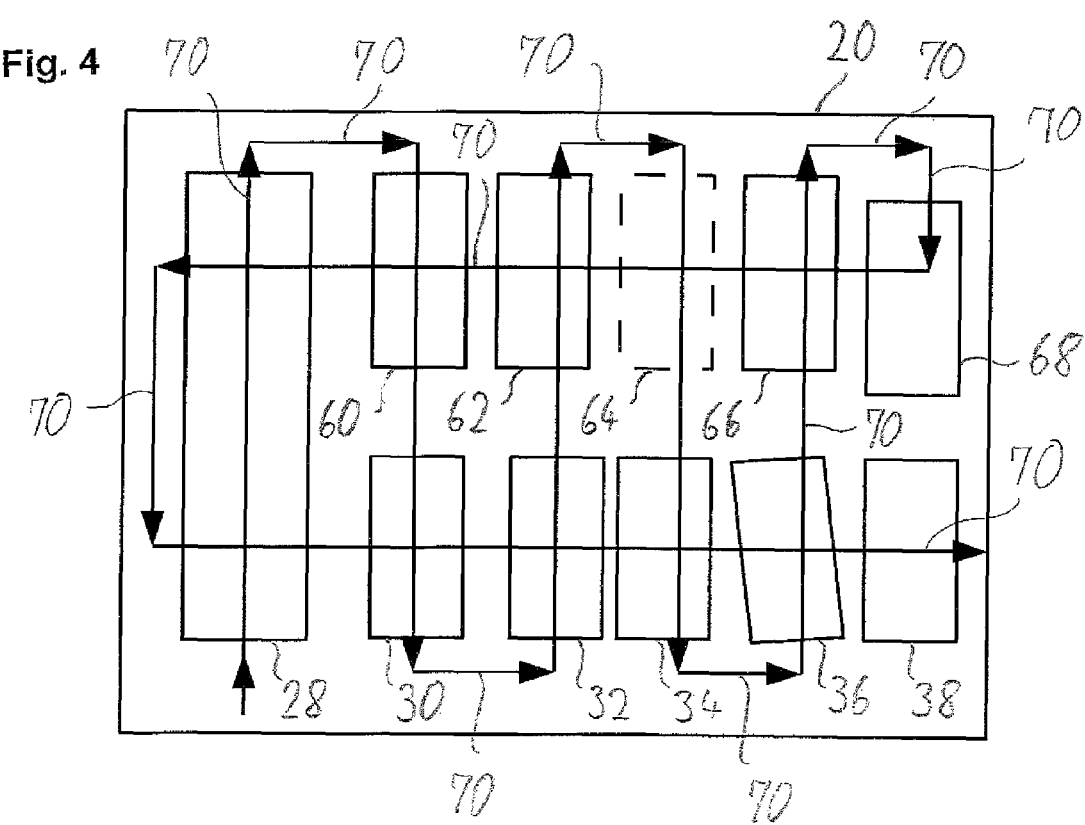
FIG. 4 is a view of the staining device shown in FIG. 3, illustrating the path of movement of a lifting device of the staining device.

In order for staining device 20 to function properly despite inaccurately positioned containers 30 through 38 and 60 through 68 and/or despite the manufacturing tolerances, the staining device is calibrated with the aid of sensor device 45. To this end, lifting device 24 carrying sensor device 45 is moved over the components of staining device 20 along a path 70 shown in FIG. 4, and specifically in such a way that sensor lever 50 of sensor device 45 repeatedly hits the individual components. Alternatively, sensor device 45 may also be moved along a different path through staining device 20.

FIG. 5 shows a flow chart of a program for calibrating staining device 20. The program is preferably started in a step S2, in which variables are initialized if necessary.

In a step S4, sensor device 45 is attached to transport device 22, specifically to lifting device 24.

In a step S6, lifting device 24 is moved through staining device 20 along the predetermined path 70, and specifically in such a way that sensor lever 50 hits the individual components of staining device 20. During this process, sensor device 45 can be moved vertically to some extent, so that once it has hit one of the components, it may be lifted, moved further, and lowered again in order for it to hit the next component.

The exact position of lifting device 24, and thus that of sensor device 45, can be detected at all times with the aid of calibration unit 23. Further, the exact positions of sensor device 45 on lifting device 24 and of sensor lever 50 on sensor device 45 are known. Thus, based on an output signal of sensor unit 48 of sensor device 45, calibration unit 23 can precisely determine where sensor lever 50 hits the components of staining device 20, so that the exact positions of the components within staining device 20 can be determined as a function of the output signal of sensor unit 48 and the current position of sensor device 45.

In a step S8, the output signals of sensor unit 48 are stored or, when the output signal exhibits an amplitude which indicates that sensor lever 50 has hit [a component], the current position of sensor lever 50, and thus that of the component hit, are stored. Each time sensor lever 50 hits one of the components, the coordinates at which sensor lever 50 is located at the time of contact are stored.

In a step S10, the positions of the components are determined. In other words, the exact positions and/or orientations of the components are determined based on the locations where sensor lever 50 has hit the components and based on the known dimensions of the components.

In a step S12, the determined positions are stored, so that sample basket or baskets 26 can be precisely moved to the individual components of staining device 20 during the operation of staining device 20.

In a step S14, the program for calibrating staining device 20 may be terminated. Preferably, the program is executed each time a component of staining device 20 has been replaced or repaired.

The present invention is not limited to the exemplary embodiments described herein. For example, staining device 20 may contain a greater or lesser number of components, the positions of which are detectable with the aid of sensor device 45. Further, a plurality of sample baskets 26 may be moved simultaneously within staining device 20, or sensor device 45 may be moved simultaneously with a sample basket 26, for example by means of an additional lifting device 24.

LIST OF REFERENCE NUMERALS 20 staining device
22 transport device
23 calibration unit
24 lifting device
26 sample basket
28 oven
30 first container
32 second container
34 third container
36 fourth container
38 fifth container
40 handle
42 holder
44 coupling member
45 sensor device
46 coupling unit
47 sensor circuit
48 sensor unit
49 base element
50 sensor lever
60 sixth container
62 seventh container
64 receiving space
66 eighth container
68 ninth container
70 path of movement
S2-S14 steps two through fourteen

What is claimed is:

1. A sensor device (45) for calibrating a staining device (20), the sensor device comprising:
   a coupling unit (46) configured to be attachable to a transport device (22) of the staining device (20) via a coupling member (44), the coupling member (44) configured to couple with the coupling unit (46) or a transport basket; and
   a sensor unit (48) carried by the coupling unit and adapted to detect the presence of movable components of the staining device (20);
   wherein the sensor unit (48) operates using acoustic, optical or tactile sensing techniques;
   wherein the sensor unit (48) includes a base element (49), a sensor lever (50) fixedly secured to the base element (49), and a sensor circuit (47) configured to detect a position of the sensor lever (50) or a force acting on the sensor lever (50).

2. A staining device (20) for staining samples, comprising:
   a sensor device for calibrating a staining device (20), the sensor device including:
      a coupling unit (46) configured to be attachable to a transport device (22) of the staining device (20)); and
      a sensor unit (48) carried by the coupling unit adapted to detect the presence of movable components of the staining device (20);
   a transport device (22) attached to the sensor device (45);
   a plurality of components (20) arranged in the staining device (20); and
   a calibration unit (23) capable of driving the transport device (22) to move the sensor device (45) through or over the components in such a way that the sensor device (45) detects the presence of the components;
   a controller configured to control the transport device (22) to carry the coupling unit (46) in place of a transport basket.

3. The staining device (20) as recited in claim 2, wherein the components include a plurality of containers (30, 32, 34, 36, 38) containing process media for processing the samples and/or an oven (28) for drying the samples.

4. A method for calibrating a staining device (20), the method comprising:
   attaching a sensor device (45) to a transport device (22) of a staining device (20) in place of a transport basket;
   moving the sensor device (45) through the staining device (20) by means of the transport device (22); and
   using the sensor device (45) to detect where predetermined movable components of the staining device (20) are located within the staining device (20).

5. The method as recited in claim 4, wherein the sensor device (45) is used to detect where containers (30, 32, 34, 36, 38) for receiving process media are located within the staining device (20).

6. The method as recited in claim 5, wherein the transport device (22) moves the sensor device (45) over and/or through the staining device (20) in such a manner that a sensor lever (50) of the sensor device (45) successively hits the different components, thereby influencing an output signal of the sensor unit (48); and further comprising the step of:
  determining the arrangement of the components within the staining device (20) based on the output signal and the current position of the sensor device (45).

* * * * *